(12) United States Patent
Elmaleh et al.

(10) Patent No.: US 9,173,569 B2
(45) Date of Patent: Nov. 3, 2015

(54) INTRAVASCULAR IMAGING DEVICE AND USES THEREOF

(76) Inventors: David R. Elmaleh, Newton, MA (US); Rick A. Rogers, Needham, MA (US); Hjalmar Brismar, Lidingo (SE)

(*) Notice: Subject to any disclaimer, the term of this patent is extended or adjusted under 35 U.S.C. 154(b) by 0 days.

(21) Appl. No.: 13/252,963

(22) Filed: Oct. 4, 2011

(65) Prior Publication Data
US 2012/0020893 A1    Jan. 26, 2012

Related U.S. Application Data

(63) Continuation of application No. 11/154,013, filed on Jun. 16, 2005, now Pat. No. 8,029,766.

(60) Provisional application No. 60/580,938, filed on Jun. 18, 2004.

(51) Int. Cl.
| A61B 5/00 | (2006.01) |
| A61B 8/00 | (2006.01) |
| A61B 10/00 | (2006.01) |
| A61B 5/02 | (2006.01) |
| A61K 49/00 | (2006.01) |

(52) U.S. Cl.
CPC ............. *A61B 5/0071* (2013.01); *A61B 5/0084* (2013.01); *A61B 5/02007* (2013.01); *A61B 5/0068* (2013.01); *A61B 5/0086* (2013.01); *A61K 49/0034* (2013.01)

(58) Field of Classification Search
USPC ........................................................ 424/9.6
See application file for complete search history.

(56) References Cited

U.S. PATENT DOCUMENTS

| 5,801,191 A * | 9/1998 | Bressi et al. .................. 514/449 |
| 6,342,221 B1 * | 1/2002 | Thorpe et al. .............. 424/178.1 |
| 6,387,350 B2 * | 5/2002 | Goldenberg ................. 424/1.57 |
| 6,843,980 B2 * | 1/2005 | Green ............................ 424/9.6 |
| 7,176,280 B2 * | 2/2007 | Hammock et al. ............. 530/324 |
| 7,989,417 B2 * | 8/2011 | De Haen et al. ............... 514/5.9 |

FOREIGN PATENT DOCUMENTS

WO    WO 9848838 A1 * 11/1998 ............ A61K 41/00

OTHER PUBLICATIONS

Ojima et al. (PNAS 1999, 96, 4256-4261).*
Tung et al. (ChemBioChem 2003, 4, 897-899).*
Ambler et al. (Bioorg. Med. Chem. Lett. 1999, 9, 1103-1108).*
Wikipedia Paclitaxel 2013.*
Wikipedia Haptens 2013.*
Beychok et al. (J. Biol. Chem. 1967, 242, 2460-2462).*

* cited by examiner

*Primary Examiner* — Michael G Hartley
*Assistant Examiner* — Melissa Perreira
(74) *Attorney, Agent, or Firm* — Peter B. Scull; Hamilton, DeSanctis & Cha LLP

(57) ABSTRACT

The invention is directed to a probe-type imaging device useful to visualize interior surfaces, e.g., the lumen of blood vessels. Specifically, the probe-type device is particularly useful for direct tissue imaging in the presence or absence of molecular imaging agents.

4 Claims, 27 Drawing Sheets

A

B

C

INTRAVASCULAR IMAGING DEVICE AND USES THEREOF

RELATED U.S. APPLICATION(S)

The present application is a continuation of U.S. patent application Ser. No. 11/154,013 filed Jun. 16, 2005, now U.S. Pat. No. 8,029,766, issued Oct. 4, 2011, which is a non-provisional of and claims priority to U.S. Provisional Application Ser. No. 60/580,938, filed Jun. 18, 2004, all of which applications are hereby incorporated herein by reference for all that they teach and suggest.

TECHNICAL FIELD

The present invention is directed to a probe-type imaging device useful to visualize interior surfaces, e.g., the lumen of blood vessels. Specifically, the probe-type imaging device is useful for direct tissue imaging in the presence or absence of molecular imaging agents.

BACKGROUND

Heart disease and stroke are the main cause of death in the United States. Most of the debilitating factors related to these diseases are rooted in vascular disorders. The main vascular insufficiencies are associated with vascular plaque formation and thrombus formation that block or decrease blood flow and, as a result, the oxygenated blood supply to these important organs. Medical device technologies and medication treatment are available to mechanically open the arteries or dilate them to avoid heart attack and stroke.

Percutaneous transluminal coronary angioplasty ("PTCA") was advanced by stents and medicated stents placement. Improvements of these methods are still required, however, to improve diagnosis and treatment of these diseases when they occur. Early detection and prevention of plaque and thrombus formation are needed to lower the incidence of first onset causing infarction and stroke; restenosis post-treatment and the efficacy follow-up of a therapy treatment.

Improvements of these methods are required to improve diagnosis and treatment of these diseases when they occur. Early detection and prevention of plaque and thrombus formation are still needed to lower the incidence of first onset causing infarction and stroke; restenosis post treatment and the efficacy follow-up of a therapy treatment.

There are a number of technologies currently in use for visualizing the lumen of vessels and diagnosing plaque, e.g., radiopharmaceuticals using PET and/or a beta probe, intravascular ultrasound (IVUS), intravascular MRI, intravascular IR, optical coherence tomography (OCT), intravascular temperature changes and their combinations. Different radionuclides are used in myocardial imaging of subjects at rest and after exercise for determining blood flow insufficiencies that indicate stenosis or measurements of other related physiological parameters. Ultrasound is used to image heart wall motion and to measure the blood ejection fraction. MRI imaging and Fast CT scanning are also used to measure similar physiological parameters that indicate stenosis. Direct measurement of plaque in the arteries uses high resolution CT imaging during a simultaneous intra-arterial injection of a contrast media that delineates the area of the narrowing of the artery during the catheterization procedure. OCT visualization of vessel involves the use of complicated and expensive instrumentation as well as the repeated saline washes to view the vessel wall.

In addition, CT, MRI and ultrasound imaging display spatial information differently from CCD light imaging. OCT disclose, in several patents, devices that are aimed at vessels and neoplastic tissue visualization. The utility of these devices is limited due to their complexity and use of mirrors, lens, and light focusing apparatuses required for light reflection propagation and visualization. Furthermore, the wall visualization requires blood washout using repeated saline flushes. Device positioning and registration require delicate and accurate guidewire 13 repositioning such as back and forth movements resulting in difficult therapy deployment.

Current imaging techniques using radiopharmaceuticals using PET and/or a beta probe, intravascular ultrasound (IVUS), intravascular MRI (IVMRI), intravascular IR, OCT, are not optimized. The current IVUS, IVMRI, intravascular IR, and intravascular thermal imaging techniques as well as the current scientific reports of in vivo molecular fluorescence tomography (MTF) (US 2004/0015062 A1 and references therein) do not teach the use of a specific intra-tissue visualization device.

As such, there remains a need for a more inexpensive and sensitive and efficient devices for direct imaging of vessel lumen.

SUMMARY OF THE INVENTION

In accordance with one embodiment of the present invention, a probe-type imaging device is provided that may be more sensitive than current methods of visualizing the vessel lumen and allows for more accurate diagnosis and improved deployments of stents or for the follow-up of therapy. The probe-type imaging device of the invention may also be useful in the early diagnosis of plaque formation, as well as in the identification of vulnerable plaque in individuals that are prone to developing it and/or patients undergoing catheterization.

In another embodiment, a catheter (or guidewire) probe-type imaging device is provided that can be useful for clear visualization of the vascular system. The probe-type device may also be useful in non-medical applications, e.g., inspection in manufacturing facilities or sewer pipe. The probe-type imaging device of the invention, in one embodiment, provides for sensitive developed light technology detection (reflection and scatter), which can be useful for the visualization and inspection of any surface, e.g., metal, biological tissue, plastic or glass, and ceramic.

In another embodiment of the present invention, a method is provided using the probe-type imaging device for direct tissue imaging in the absence of a molecular imaging agent, e.g., contrast media. Alternatively, a method is provided using the probe-type imaging device for direct tissue imaging in combination with a molecular imaging agent(s). The use of molecular imaging agent for blood and/or tissue enhances tissue visualization. The method provided in connection with the present invention can reduce potential toxic effects of molecular imaging agents' on a subject, as the concentrations required for contrast media using the probe-type imaging device of the invention are lower than the concentrations of contrast media required by existing imaging techniques. To that end, the probe-type imaging device of the invention may be useful for intra-tissue inspection.

In another embodiment, the probe-type imaging device of the invention utilizes photon detection enhancement as a function of changing the detected wavelength as compared to the emitted one. In doing so, the probe-type imaging device of the invention may be used to generate real-time tissue imaging, e.g., imaging and assessment of the vascular lumen, the cap and its thinning in vulnerable plaque. In addition, the probe-type device of the invention may be useful for precise stent deployment, when used alone, or in combination with other diagnostic modalities for drug delivery or, for instance, the delivery of a gene vector (e.g., viral vector) for gene therapy.

In another embodiment, the present invention provides a disposable imaging probe that is simple to use and that is relatively accurate. Unlike existing devices, the probe-type imaging device of the invention does not require the use of mirrors, lenses, or light focusing apparatuses for light reflection propagation and visualization.

In a further embodiment, the probe-type imaging device of the invention, unlike the other devices, such as that disclosed in U.S. Pat. No. 6,485,413 B1 and references cited therein, provides certain advantages, uses a multiple laser light source and does not require a focusing element. The direction and scope of the emitted light projected by the probe-type imaging device of the invention differs from other intravascular imaging devices, as light does not have to be redirected. The probe-type imaging device of the invention does not require the use of mirrors and simplifies concentration and cost. Specifically, the probe-type imaging device of the invention provides a detector array layout for efficient analysis of reflected and/or scattered light detection (the layout of detector allow detection of the vascular wall and its surroundings from different angles and views). In this manner, the probe-type imaging device can be applied to any catheter or guidewire 13.

In one embodiment, the probe-type imaging device of the invention may be provided with signal enhancement detection (using deferential wavelength for emission and detection in combination with nanocrystal light manipulation). To this end, data acquisition and signal analysis and presentation may be implemented. Signal enhancement detection may further be implemented by using contrast media for specific enhancement of blood components for vessel lumen or vessel wall.

In another embodiment, the method of the present invention, unlike those currently available using MFT, such as those disclosed in U.S. Pat. No. 6,081,322 and US 2004/0015062 A1 and references cited therein, do not focus on general in vivo imaging. Such imaging methods are limited, as potential non-accurate assessment of the image collection is due to light absorption and scatter evolved with depth (low resolution and sensitivity). Rather, the method of the present invention takes advantage of the absorption and scatter properties to provide a method for visualization of intravascular tissue and tissue border removal in neoplastic surgery, such as that associated with a subject undergoing surgery in the intestine or renal system.

In another embodiment, the device and methods of the invention may be used in combination with other detection methods such as thermal and beta probe. The probe-type imaging device of the invention may also be particularly useful in procedures that require shorter tissue depth inspection as the disclosed device is able to delineate minute abnormal tissue. In one embodiment, the probe-type imaging device of the invention may be used for a more localized therapy deployment, such as, stent, laser for plaque abolition or vascular wall stripping. Hydrostatic pressure, piezio electric crystal, or other mechanical device may be useful to advance the probe-type imaging device detectors along a lumen, e.g., a vessel lumen.

The vascular vessel wall and their components including arteriosclerosis and vulnerable plaque have a limited depth of a few microns to a few millimeters and the use of light has several advantages for direct viewing and measure depth and thickness. In one embodiment, the probe-type imaging device is used to measure the time-of-flight from scattered light. In one embodiment, the probe-type imaging device of the invention may be useful in the measurement of time-of-flight of scattered light where the light detectors have at least about from about 0.1 picoseconds to about 3 picoseconds resolution.

The probe-type imaging device of the invention and methods of use thereof overcome the limitations of other known imaging methods by providing for: 1) a light and/or scatter measurement of the intravascular system; 2) variable wave length for testing; 3) real-time read of wall thickness; 4) real-time imaging of the vascular lumen system; 5) a probe size that useful for stent or medication deployments; 6) increased sensitivity due to enhanced light and scatter; and 7) a 3D visualization of the vessel lumen.

The methods provided herein may be used to enhance the diagnosis and treatment of the tissue disorders, for example, a disorder of the cardiovascular system, such as, arteriosclerosis, atherosclerosis, or vessel aneurysm.

BRIEF DESCRIPTION OF THE DRAWINGS

The invention will be further understood from the following description with reference to the figures, in which:

FIG. 19A, is a photograph showing a fiber-optic probe on the luminal surface of aortic tissue. FIG. 19B, is a photograph showing an intensity graph micropgraph of scattered light around a secondary vessel (darker region).

DETAILED DESCRIPTION OF SPECIFIC EMBODIMENTS

Figure 1:
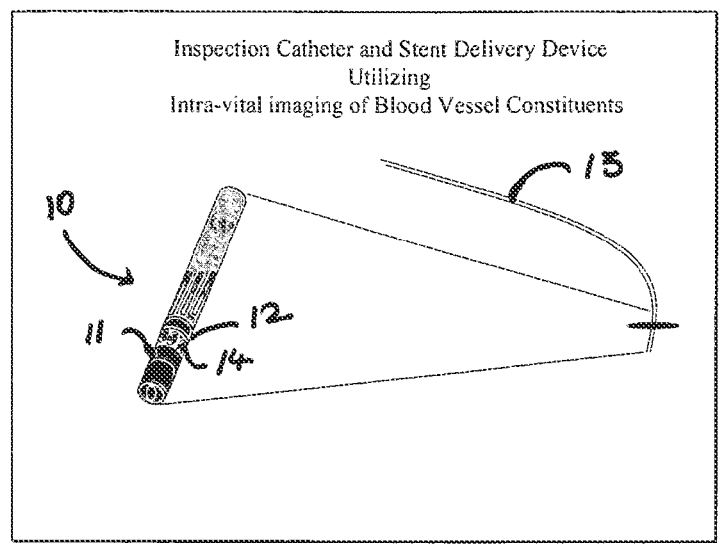
FIG. 1 is a schematic diagram of one embodiment of a probe-type imaging device of the invention where a probe assembly is mounted on catheter end.

Referring now to FIG. 1, there is shown a schematic diagram of a probe-type imaging device 10 in accordance with one embodiment of the invention. The device 10, in one embodiment, includes a probe assembly 11 mounted on one end of the imaging device 10. The probe assembly 11, in one embodiment, may be designed to emit radial illumination. As shown in FIG. 1, the probe assembly 11 may include a body through which light may be transmitted along a guidewire 13, and on which photonic detectors may affixed. The body 12 of the probe-type imaging device 10 can be any shape and dimension suitable for imaging within a vessel. In one embodiment, the body 12 of the probe-type imaging device 10 is shaped as a tube. The guidewire 13, useful in the probe-type imaging device 10 of the invention, can be of any type, size or dimension suitable for guiding the probe-type imaging device 10 of the invention. In one embodiment, the probe-type imaging device 10 of the invention has more than one photonic detector. The photonic detectors 14 can be affixed in any pattern suitable for the detection of emitted light. In one embodiment, the photonic detectors 14 may connected to one another so that electrical signals can be received by each photonic detector and signals from each photonic detector can be received in an integrated fashion. The photonic detectors 14 can be of any size, shape, or dimension suitable for imaging. It should be noted that the probe-style imaging device 10 of the invention may be disposable.

An external cabinet (not shown) may be provided within which necessary optical, electrical and signal processing equipment (i.e., the receiving system) may be located along with a visual display (not shown) terminal freely positionable (i.e., remotely located) for optimal use in the procedure area. Light may be provided to the probe-style imaging device 10 of the invention from a light source. The light may be emitted from the probe-style imaging device 10 to illuminate a surface. In turn, emitted light contacts the surface and is then scattered and reflected back to a photonic detector on the probe-style imaging device 10. The photonic detector may be designed to convert the scattered and reflected light into an electrical signal. The electrical signal from the photonic detector may be transmitted to a receiving system, e.g., signal processing equipment (not shown), that converts the signal(s) into information using, for instance, a mathematical algorithm(s). The information resulting from the conversion of the photonic detector signal(s) can be displayed on a viewing screen as described below.

Figure 2:
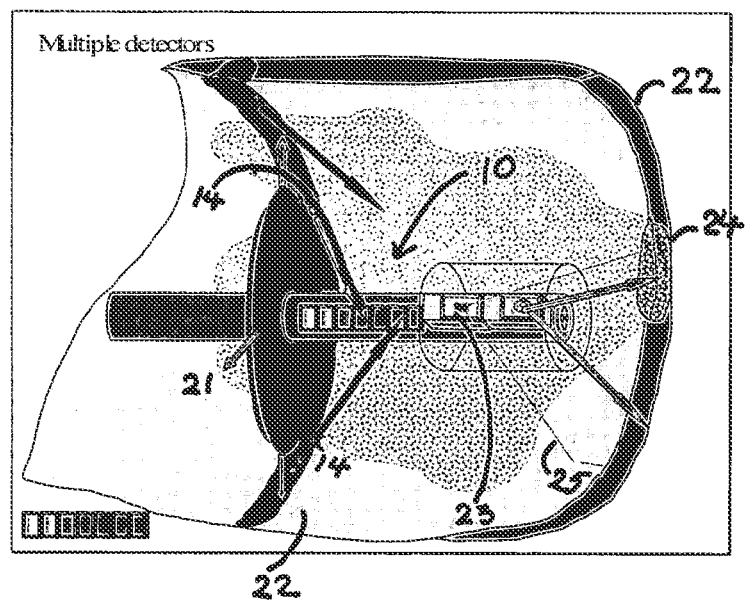
FIG. 2 is a schematic diagram of one embodiment of a probe-type imaging device of the invention utilized to inspect a vessel wall.

In one embodiment, the probe-type imaging device 10 may be useful for inspecting surfaces, e.g., a vessel wall. FIG. 2 illustrates a schematic diagram of the probe-type imaging device 10 having multiple photonic detectors 14 utilized to inspect a vessel wall 22. As shown in FIG. 2, a disk of light 21 illuminates the vessel wall 22. Signals from the multidetectors 14 may be displayed in real-time on a view screen used by the cardiologist. Real-time viewing of vessel features enables accurate and precise positioning and deployment of therapeutic interventions such as stents and phototherapy. Scattered light and reflected light from the vessel wall 22 may be picked up by the detectors 14. While the optical illumination assembly is not shown in FIG. 2, single photon array detector 23 may measure time-of-flight of photons colliding with tissue features in plaque 24 (light colored speckled region) and in normal vessel wall 22 (solid gray colored region). In this manner, vessel dimensions and position of occlusions, partial blockages and vessel wall 22 protrusions can be revealed. Digital maps of the catheters position relative to anatomical landmarks can also be recorded and projected as 3-D vectors. Secondary measurements from back scattered photons 25 can give information of vessel wall 22 thickness. Diseased regions may be highlighted on the display screen and marked for more precise investigation. Light, diffusely scattered within tissue can reveal plaque location, plaque margins and plaque type. Light, directly reflected from vessel wall 22 surfaces can provide information about the physical characteristics of endothelial cells as well as cap composition of vulnerable plaques.

Figure 3:
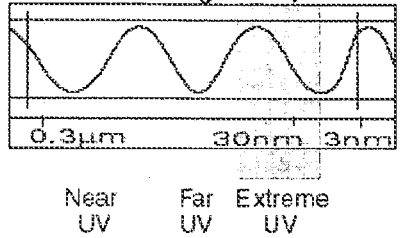
FIG. 3A is a schematic diagram of the ultraviolet region of the electromagnetic spectrum.
FIG. 3B is a schematic diagram of the visible light region of the electromagnetic spectrum.
FIG. 3C is a schematic diagram of the infrared region of the electromagnetic spectrum.
Figure 3:
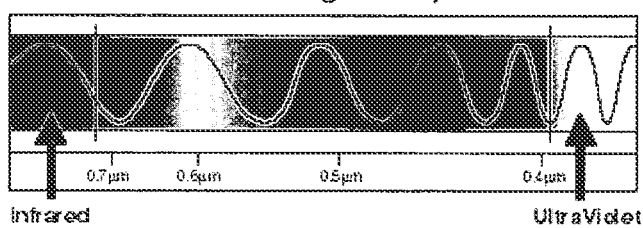
Figure 3:
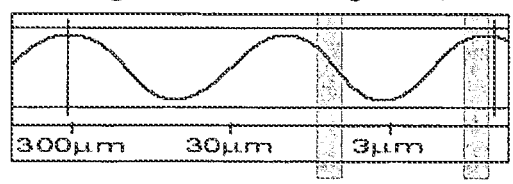

As shown in FIG. 3A-C, the light that passes through the body of the probe-type imaging device 10 can be of any wavelength suitable for imaging. In one embodiment, the wavelength of light passing through the body of the probe-type imaging device 10 may be in the visible region of light (FIG. 3A). The wavelength of light passing through the body of the probe-type imaging device 10 may also be in the ultraviolet region of light (FIG. 3B), or the infrared region of light (FIG. 3C). The light may be visible light and/or near IR light from CW diode or picosecond pulsed laser diodes. In one embodiment, a pulsed laser light source may be used in combination with single photon array detectors 23 (SPAD) of FIG. 2 affixed to the probe-type imaging device 10. This configuration may be particularly useful for detection in time-of-flight feature of the probe-type imaging device 10. In one embodiment, a time-correlated single photon counting (TC-SPC) measurement setup may be used for analysis of photonic detector signals from the probe-type imaging device 10.

Figure 4:
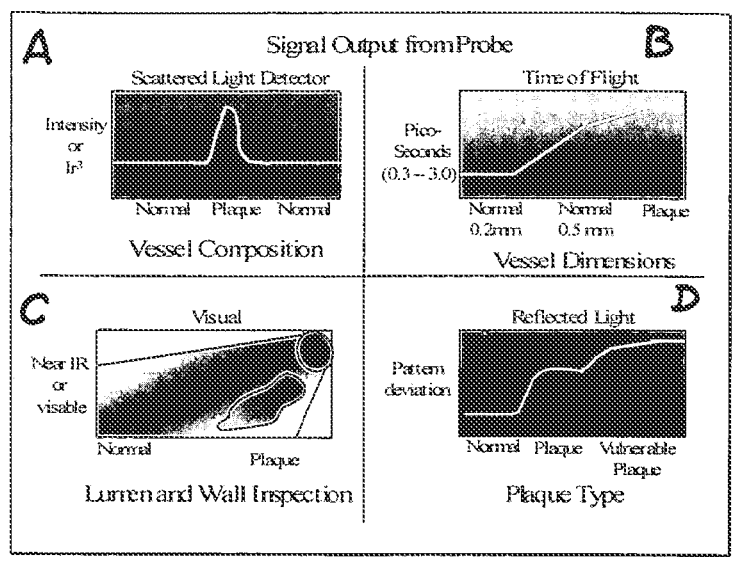
FIG. 4A is a graph showing the relative scattered light intensity signal observed in normal vessel tissue and vessel plaque using a probe-type imaging device of the invention.
FIG. 4B is a graph showing the relative time-of-flight of photons observed in normal vessel tissue and vessel plaque using a probe-type imaging device of the invention.
FIG. 4C is a schematic diagram showing an image of normal vessel tissue and vessel plaque detected with a probe-type imaging device of the invention using near infrared or visible light.
FIG. 4D is a graph showing the pattern of deviation of reflected light observed in normal vessel tissue, vessel plaque, and vulnerable vessel plaque using a probe-type imaging device of the invention.

As detailed above, and further illustrated in FIGS. 4A-D, the probe-type imaging device 10 of the invention may be used to visualize tissue features, e.g., normal vessel tissue versus vascular plaque. As shown in FIG. 4, signal from the probe 11 may be placed on view screen and recorded digitally. FIG. 4A, illustrates a graph showing the relative scattered light intensity signal observed in normal vessel tissue and vessel plaque using the probe-type imaging device 10 of the invention. FIG. 4B, illustrates a graph showing the relative time-of-flight of photons observed in normal vessel tissue and vessel plaque. FIG. 4C, illustrates a schematic diagram showing an image of normal vessel tissue and vessel plaque detected with the probe-type imaging device 10 of the invention using near infrared or visible light. FIG. 4D, illustrates a graph showing the pattern of deviation of reflected light observed in normal vessel tissue, vessel plaque, and vulnerable vessel plaque using the probe-type imaging device 10 of the invention.

Surface features of a vessel may be inspected and revealed by various detectors. Many different types of photonic detectors 23 can be affixed to the probe-type imaging device 10 of the invention, e.g., time-of-flight detectors, scattered light detectors, reflected light detectors. The probe-type imaging device 10 of the present invention may have a single type of photonic detector 23 affixed to the device 10, or a combination of different photonic detector 23 types affixed to the device 10. Any detector suitable for imaging may be useful with the probe-type imaging device 10 of the invention. As detailed below in Table 1, time-of-flight provides information on vessel dimensions and possible wall 22 protrusions into vessel lumen. Time-of-flight may be useful to give information relating to vessel wall 22 thickness in healthy tissue. Scattered light detectors 14, on the other hand, may be useful in revealing plaque location and type and plaque margins. Reflected light detector may be useful in visualizing surface features of vessel wall 22, and to identify plaque type. Direct observation can be useful to guide the probe-type imaging device 10 of the invention. A vector-based 3-D projection of the vessel, as seen from an outside oblique orientation, gives anatomically accurate reference to vessel wall 22 features and highlights suspect areas and labels diseased regions.

TABLE 1

| Vessel Composition | Probe Features | | | |
| --- | --- | --- | --- | --- |
| | Time-of-flight | Scattered Light | Reflected Light | Direct Observation |
| Normal | Reference | + | Reference | Reference |
| Plaque | + | ++ | ++ | + |
| Vulnerable Plaque | + | +++ | +++ | + |

The probe-type imaging device 10 of the invention can be used for insertion into a lumen, i.e., the cardiovascular system, at medically standard access points (femoral artery, etc.). In one embodiment, the probe-type imaging device 10 of the invention may be designed for bodily insertion and adhere to the standard coatings and materials used in catheter construction. Catheters useful in the methods of the invention can be of any length, depending on the procedure involved. In one example, it can be about 3-6 feet in length.

Figure 5:
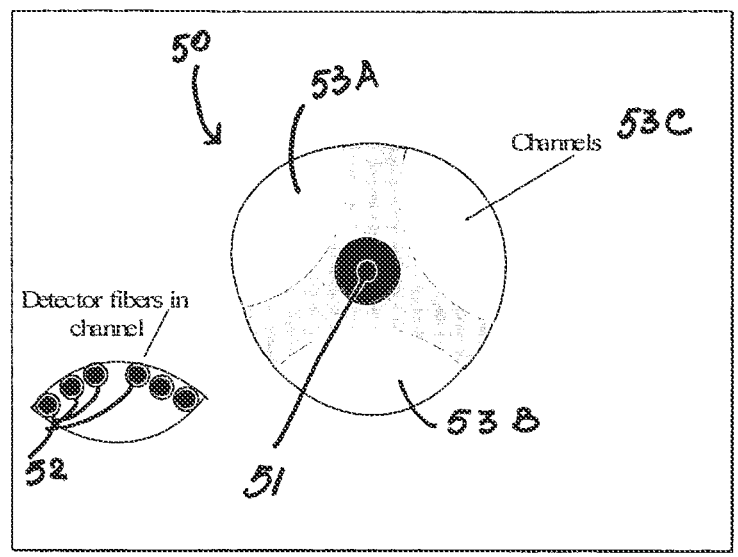
FIG. 5 is a cross-sectional view of the probe-type imaging device of the invention.
Figure 6:
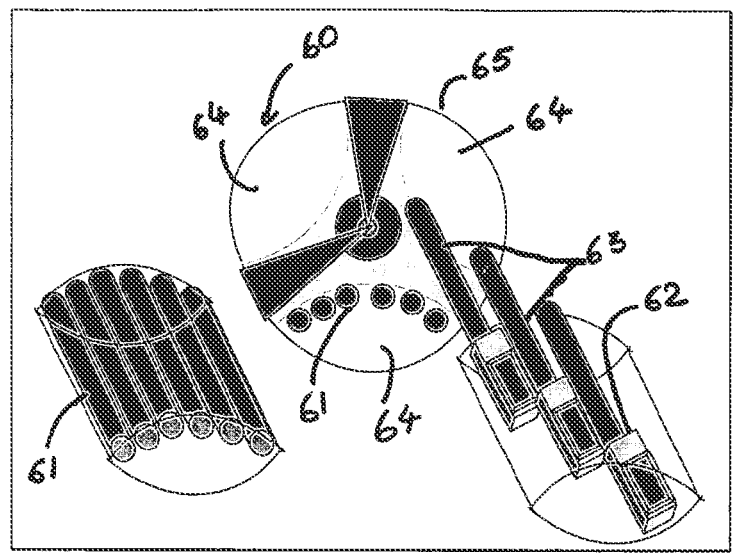
FIG. 6 is a schematic diagram showing a probe-type imaging device in accordance with another embodiment of the invention. A cross-sectional view is shown at center. An oblique view of a fiber transmission bundle within a trunk region of the device is shown at left. Right side image shows oblique view of diodes/detectors in a detector assembly on the device. Illumination from central core used to generate optical signal and appears as triangles.

The present invention, in an embodiment may provide a central, single mode coaxial fiber to deliver light to the distal end of the probe, as illustrated in FIG. 5 and FIG. 6. FIG. 5 is a schematic diagram showing a cross-sectional view at a position along a section of the probe-type imaging device 50 of the invention. The diameter of the device 50, in an embodiment, may be about 2 French. A central coaxial or single mode fiber 51 delivers light to distal end and to detector assemblies (not shown). Three grooves act as channels 53A-C for optical fibers and wires 52 to/from the detector assembly.

FIG. 6 is a schematic diagram showing one embodiment of the probe-type imaging device 60 of the invention. A cross-sectional view of the probe-type imaging devise 60 is shown at center. In one embodiment, the cross-sectional diameter of the probe-type imaging device 60 may be about 2 French or less. An oblique view of a fiber transmission bundle 61 is shown at left. In one embodiment, a small area detector 62 In/GaAS may be mounted either directly on the catheter and coupled to an optic fiber drawn parallel to the delivery fiber 61. In another embodiment of the invention, the small area detector In/GaAS may be remotely coupled to an optic fiber drawn parallel to the delivery fiber. Imaging can be performed either by bundling a large number of detectors 14/fibers along the device 10 or by rotating the device 10 with a single detector. The right side image in FIG. 6 shows an oblique view of diodes/detectors 63 in the detector assembly. Illumination from a central core may be used to generate optical signal and appears as, for instance, triangles. Three outer-grooves 64 in the device sheath 65 act as channels for fiber transmission bundle of optical fibers and wires to/from the detector assembly. The probe 60 may include features and components for stent deployment.

Detection and Analysis Features

A. Scattered-Light Probe

Figure 7:
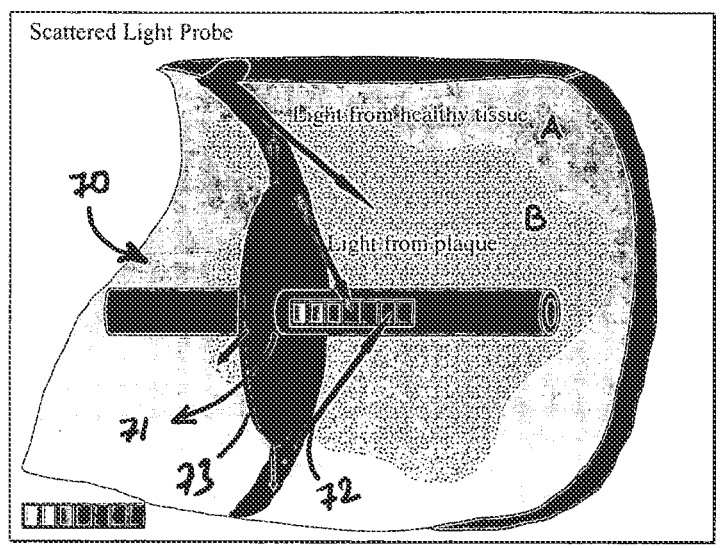
FIG. 7 illustrates a schematic diagram of one embodiment of a probe-type imaging device of the invention utilized to inspect a vessel wall.
Figure 8:
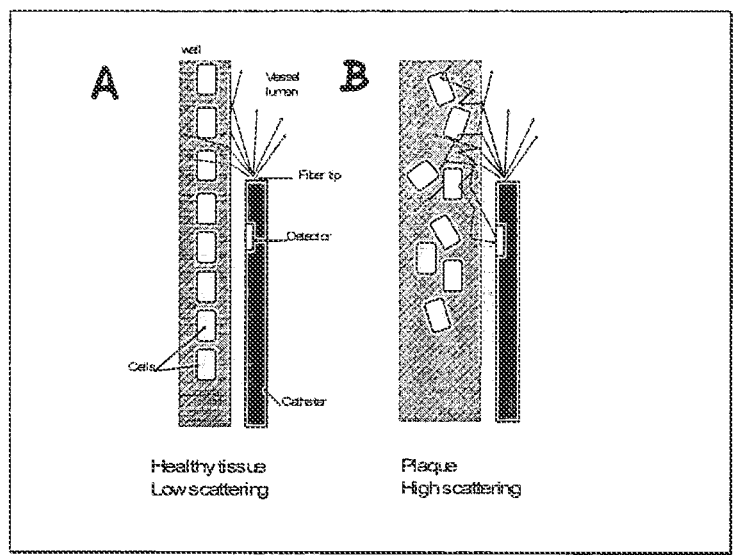
FIG. 8A-B are a schematic diagram a probe-type imaging device utilized to inspect a vessel wall.

In one embodiment, the probe-type imaging device of the invention may be a scattered-light-based probe 70. As illustrated in FIG. 7, a point source such as circular gap 71 mode fiber can scatter light 73 to the tissue and may be detected by single or multiple photodetectors 72 embedded on catheter surface. FIG. 8A, shows the low scattering of light observed from normal vessel tissue. FIG. 8B, shows the high scattering of light from vessel plaque. As shown in FIG. 7, and further illustrated in FIGS. 8A and 8B, a plaque B typically has a lower optical density, because it has more misaligned subcellular features and increased disorder than does normal vessel wall tissue A, and will give an increased diffuse light intensity relative to normal tissue. Light is scattered due to inelastic collisions between photons and tissue. Normal tissue, on the other hand, typically has a relatively well ordered structure with cells aligned along the vessel wall 22. Extracellular matrix exhibits well defined collective orientation. In plaque, the structure is chaotic with large amounts of extracellular material with poor orientation and cells with random orientation. Light scattering in those two situations is different, often with several orders of magnitude of change. In healthy tissue, small amounts of light will be scattered and the tissue will have a more transparent appearance. The diffuse scattering properties can be measured as the amount of backscattered light. Plaque scatters significantly larger amounts of light than does healthy tissue. Regions of diseased tissue may be identified by changes of light intensity and distance from the probe source.

Intensity of back-scattered light (I) at various distances r from the point of entry of light, and the product of Ir3 is plotted semi logarithmically against r. The fractional change in optical mean free path (l) can be determined from the following equation (d l/l=(1+2rs)−ld F(r,l) as referenced in the paper: Miki H, Rogers R A, Lehr J, Butler J P. Geometric hysteresis in pulmonary surface-to-volume ratio tidal breathing. J Appl Physiol 1993; 75(4):1630-1636.

Near IR light may be used as the penetration depth for IR can be higher than for visible light, and the amount of back-scattered may thus be lower. A high sensitivity detector, SPAD—avalanche photodiode, can be used to detect even small amounts of back-scattered light. Source and detector may be attached to a light frequency modulator. By making rapid adjustments in frequency, scattered light of various wavelengths can detected. Furthermore, reflected light can be picked up and transmitted via the same assembly. In one embodiment, light diffusers may be used to deliver illumination light of appropriate frequency from the catheter to the vessel wall 22. Nanocrystals may also be embedded in the central core function as light diffusers. If embedded in the outer cladding of the catheter, physical properties of nanocrystals will be used as light amplifiers and specific wavelength detectors. Examples of light diffusers in the public domain are waveguide cavities, cracks in the fiber and coaxial coating, and mirrors.

Figure 9:
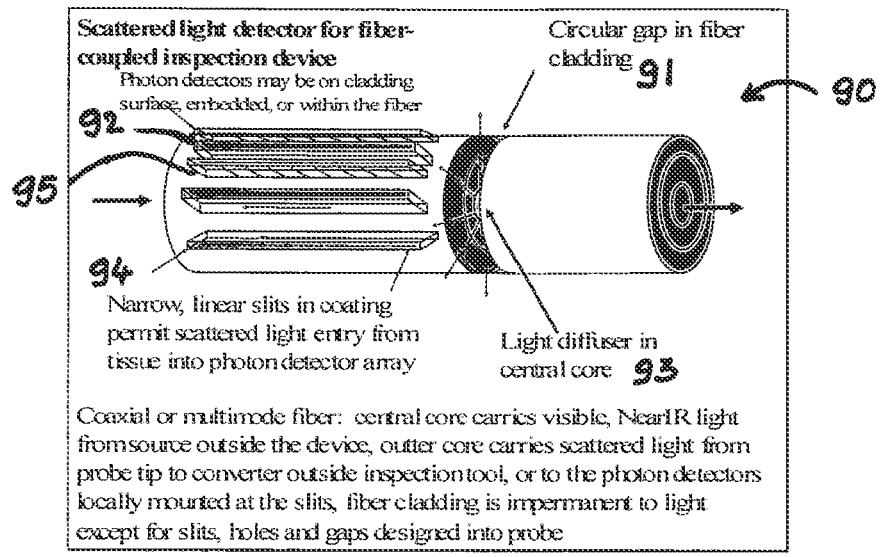
FIG. 9 is a schematic diagram showing a probe-type imaging device in accordance with an embodiment of the invention.

In one embodiment, the light emitted from the probe-type device of the invention may be emitted from an angled feature to the surrounding surface, e.g., tissue. In another embodiment, the light emitted from the probe-type device of the invention may be emitted from a the fiber end to the surrounding surface, e.g., tissue. As illustrated in FIG. 9, in one embodiment, the light emitted from the present probe-type imaging device 90 may be emitted from a circular gap 91 to the surrounding surface, e.g., tissue. Source and detector 92 may be attached to a light frequency outside the device 90. By making rapid adjustments in frequency, scattered light of various wavelengths can be detected. Furthermore, reflected light can be picked up and transmitted via the same assembly. In one embodiment, nanocrystals embedded in central core 93 function as light diffusers and re-direct light toward vessel wall to give spherical illumination. Inspection tool can be tuned to detect scattered or reflected light and to specifically detect emission spectra from exogenously applied fluorescent dyes.

In one embodiment, the probe-type imaging device can integrate thereinto detector arrays 94 in flexible sheets, offset and wrapped around the length of the device, with each sheet 94 containing multiple photodiode detectors in a packed array 95 organized as diagonal, strip, cross, ring or other configuration. Each photodiode 95 may be bounded with LED strips for illumination. Diodes 95 can be photon counting and intensity sensing.

B. Reflected-Light Probe

Figure 10:
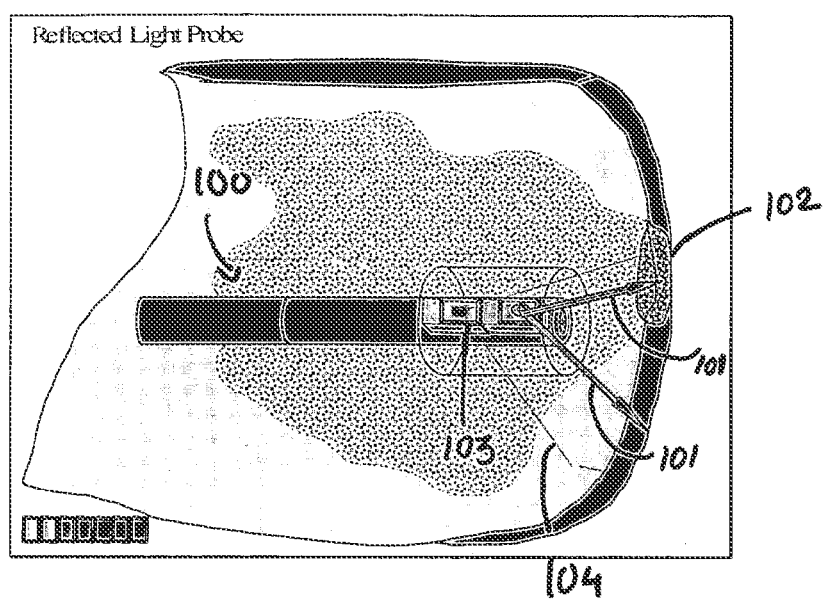
FIG. 10 is a schematic diagram showing one embodiment of a probe-type imaging device of the invention.

In one embodiment, the probe-type imaging device of the invention can be a reflected-light-based probe 100 as illustrated in FIG. 10. A reflected-light probe 100 of the invention may be used to provide information about plaque and plaque cap covering vulnerable plaque. As shown in FIG. 10, during operation, a photon stream 101 may be released from a point source, and after striking a tissue surface 102, may be reflected back 104 to detector(s) 103. Signal intensity may be generated from the number of photons counted. Light reflected from normal tissue will have a significantly different reflected light signal from tissue within a plaque.

Figure 11:
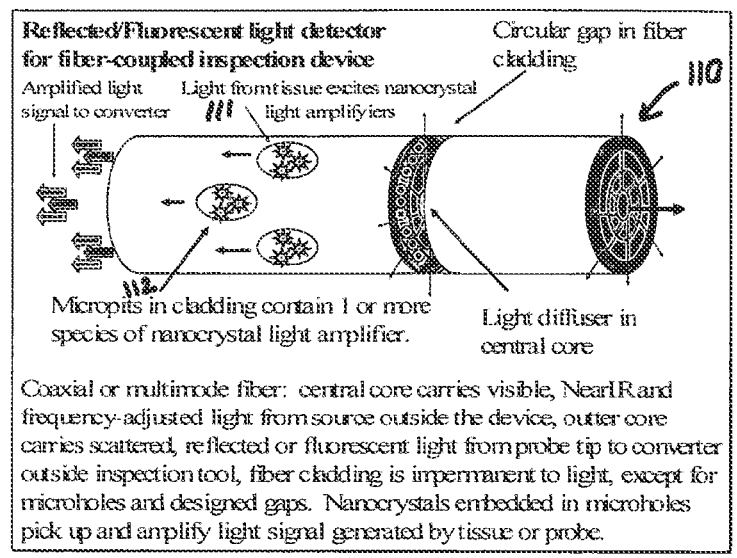
FIG. 11 is a schematic diagram showing one embodiment of a probe-type imaging device of the invention.

As illustrated in FIG. 11, in one embodiment, the light source and detector on probe-type imaging device 110 may be coupled to a light frequency modulator (not shown). This configuration can be used to make rapid adjustments in frequency, so that light of various wavelengths can be detected by the probe-type imaging device 110 of the invention. Furthermore, reflected-light can be picked up and transmitted via the same assembly. In an embodiment, nanocrystals 111 may be embedded in outer cladding 112 function to act as specific wavelength detectors. Inspection tool can be tuned to detect scattered, reflected and to specifically detect emission spectra from exogenously applied fluorescent dyes or other compounds bound to specific structures on and within vessel walls.

C. Time-of-Flight Probe

Figure 12:
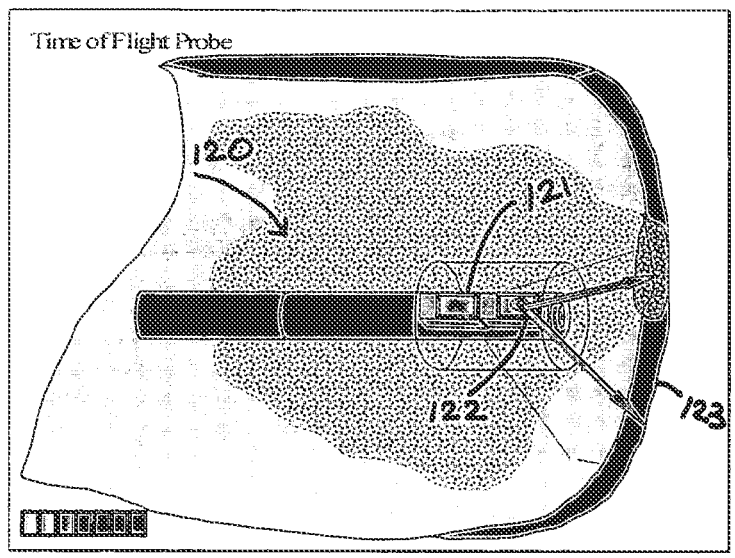
FIG. 12 is a schematic diagram showing one embodiment of a probe-type imaging device of the invention.

In one embodiment, the probe-type imaging device of the invention may be design as a time-of-flight probe 120 as illustrated in FIG. 12. In this configuration, the probe-type imaging device 120 can be used to measure time-of-flight of scattered light where light detectors 121 have at least about 3 picoseconds resolution. In another embodiment, the probe-type imaging device 120 can be designed to measure time-of-flight of scattered light where the light detectors 121 have at least about 0.1 picoseconds resolution.

In this case, single photons may be released from a point source 122 and the time-of-flight before the photon is re-detected may be measured. Photons traveling through, for instance, thick tissue 123 will take more time (picoseconds). Time-of-flight measurements may be used to determine the total distance a photon travels before reaching a detector. The distribution of traveling times for a large number of photons can reveal information about the scattering properties of the material. In weakly scattering materials, detected photons have a low probability of inelastic collisions and the majority of backscattered photons have only collided once, resulting in a single narrow distribution of travel times. In highly scattering materials, the detected backscattered photons have a wider distribution of travel times, as the may undergo multiple collisions, resulting in a wide spread of travel distances and times. The average travel distance can, however, be shorter in highly scattering materials due to a higher probability for collision. This calls for an analysis of the distribution of travel times, and in certain tissues (plaque), the experiment can be tuned into giving multimodal distributions of travel times that can be analyzed as multiscatter events compared to a single modal distribution for weakly scattering materials (healthy tissue).

Figure 13:
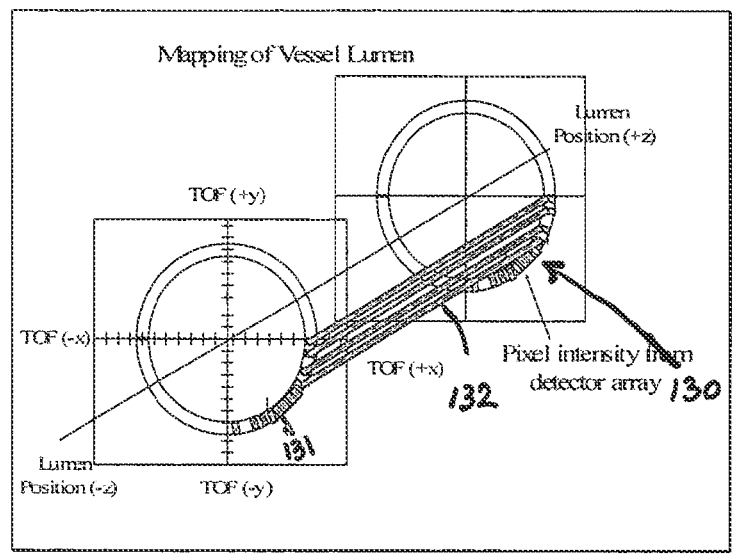
FIG. 13 is a schematic diagram illustrating how time-of-flight is used to measure the time intervals (picoseconds) from pulsed light source from a disc shaped opening.

FIG. 13 illustrates a schematic diagram of how time-of-flight may be used to measure the time intervals (picoseconds) from pulsed light source from a disc shaped opening. A detector array 130 may be arranged to pick up first entry of photons for each point detector 131. Many (in this example, 50) detectors 131 can be arranged in the detector array 130, or arranged in multiple grooves 132, e.g., 3 to 4 grooves. The intensity of each detector 131 can generate a pixel map, as the device is moved down the vessel lumen. Time-of-flight gives the shape, while scattered and reflected light can reveal the nature and distribution of the plaque.

D. Optical Imaging Probe

Figure 14:
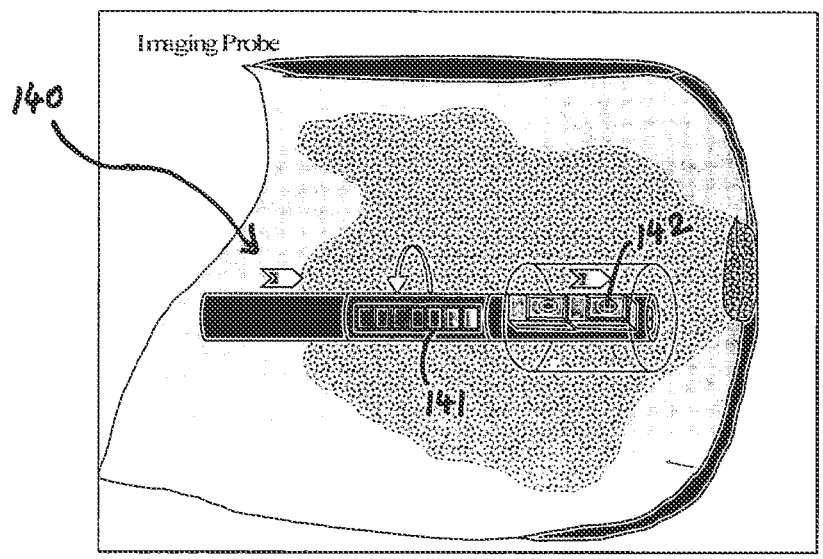
FIG. 14 is a schematic diagram showing one embodiment of a probe-type imaging device of the invention.

In one embodiment, the probe-type imaging device of the invention may be used as an optical imaging probe 140, as illustrated in FIG. 14. In such an embodiment, the optical imaging probe 140, may have a diameter of at least about 0.5 mm, and may be about 1 mm to about 2 mm. The central coaxial (not shown) fiber of the optical image probe 140 in one embodiment, may have a circumference of at least about 3 mm, and may be from about 5 mm to about 7 mm. In one embodiment, more than about 40 photon detectors 141 may be affixed to the surface of the optical imaging probe 140. The pattern for which the array of detectors 141 may be arranged can similar to that illustrated in FIG. 14 or circumferentially about the probe, e.g., in a ring or wrap-around pattern, such as that shown in FIGS. 15 and 16. The ring pattern can be a series of rings on the surface of the optical imaging probe 140. In one embodiment, a light source 142 may be proximal to detector array 141 on optical imaging probe 140 and may be provided with multiple wavelengths. The detector array 141, in an embodiment, can be designed so that it rotates to enable optical imaging of local environment, while the light source 142 and catheter may remain stationary or rotate to enable optical imaging of the local environment. Visual information may be encoded and can be presented in real-time. A 3-D vector diagram of the vessel wall may be projected for plaque mapping and is useful as a reference.

Figure 15:
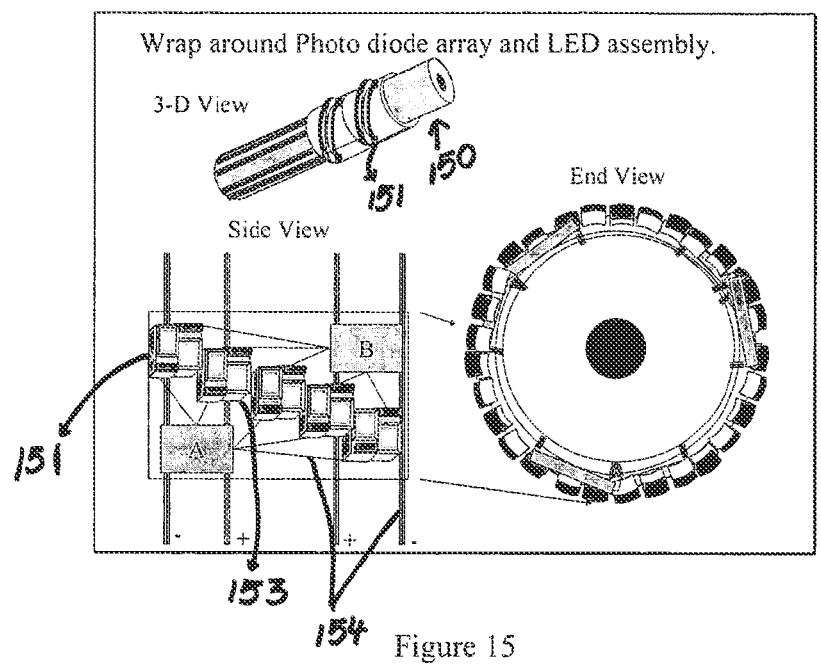
FIG. 15 is a schematic diagram showing one embodiment of a probe-type imaging device of the invention with a wrap-around photo-diode array and LED assembly.
Figure 16:
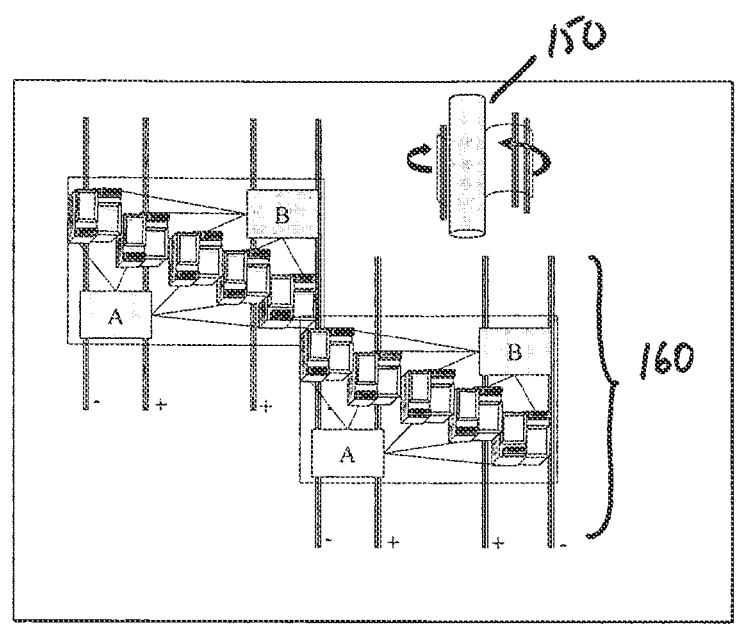
FIG. 16 is a schematic diagram showing one embodiment of a probe-type imaging device of the invention wherein wrap-around detector assemblies are fitted to catheter with staggered fit to produce a continuous spiral of detectors forming a 360 degree filed of view.

In accordance with one embodiment, the light source 142 may be provided with a wrap-around photo diode array and LED assembly 151 as shown in FIG. 15. The diodes array 151 can be placed in any pattern suitable for imaging (e.g., a diagonal, strip, cross, or other geometric pattern). In one embodiment of the invention, integrators and signal processors 153 may be alternated in the wrap-around photo diode array, with electrical leads 154 overlapping and interconnecting adjacent assemblies. Wrap-around detector assemblies 160, as shown in FIG. 16, can be positioned in a staggered pattern on the device 150 to produce a continuous spiral of detectors forming a 360 degree field-of-view as illustrated in FIG. 16. In this manner, the detector assembly 160 can be advanced forward as the device 150 is rotated. The rotation and advancement mechanism may be mechanical, hydraulic, crystalline or electronic means, e.g., piezo crystal. Alternatively, the detector assembly 160 may remain stationary.

Fluorescence and Contrast Media

Molecular imaging in one embodiment, combines molecular agents with imaging tools to capture pictures of specific molecular pathways in the body, particularly those that are key targets in disease processes. Molecular imaging holds a unique potential of simultaneously being able to find, diagnose and treat disease in vivo, as well as the ability to depict how well a particular treatment is working. The probe-style imaging device of the present invention, in an embodiment, may be used in molecular imaging techniques. The invention provides methods for molecular imaging using the probe-style device of the invention in combination with molecular imaging agents, e.g., fluorescence and contrast media.

In accordance with an embodiment, the probe-type imaging device 10, such as that illustrated in FIG. 1 of the invention may be used in the examination of structural and compositional features innate to the vessel, and may be used with exogenously applied or delivered probes of chemical, fluorescent, molecular, ionizing or radioactive origin. The probe-type imaging device of the invention can be tuned to detect scattered, reflected and to specifically detect emission spectra from exogenously applied fluorescent dyes.

Fluorescence and chemoluminescence chromophores and light excitation in the following wavelength can routinely be used both in vitro and ex vivo for diagnosis to delineate cells, cell tracking, cell components and molecular structures and other imaging related research investigation. Photodynamic therapy and near infrared fluorescent in vivo imaging received special interest in recent years. Many recent reports claim improved imaging methods in the infrared fluorescence and using new chemical preparations. In vivo imaging using these techniques initiated the design of new imaging devices such as, Molecular Fluorescence Tomography.

At present, without significant technology improvements, most if not all the proposed fluorescence imaging have limited use. A few factors determine their adoption and their widespread use as a beneficial diagnostic imaging modality in the clinic. One factor contributing to the utility of a fluorescent imaging modality may be the nature of the fluorescent compound and its activation wavelength. The targeting and adequate concentration in the diseased tissue as compared to its environment (target to non target ratio) contributes to the utility of a fluorescent imaging modality. The type of excitation light and its in-depth penetration that allows for 2D or 3D image collections, as well as the properties of the imaging device (sensitivity and resolution as a function of depth) can limit the utility of a fluorescent imaging modality.

More difficult factors are associated with the nature of the specific disease and/or the physiological parameter to be measured. In vivo situation of administered molecular probes, such as contrast agents, in conjunction with current imaging technologies may be limited due to the following:

Potential toxicity due the necessary large concentration of fluorescence contrast media required to delineate specific tissue.

The mechanism for trapping and washout has to be identified prior to its acceptance (in vivo stability, metabolite identification).

The characteristics of the specific binding and pharmacokinetics of the fluorescence agent.

Similar obstacles were encountered in developing MRI contrast agents that have longer in vivo half-life in tissue.

The probe-type imaging device of the invention may also be useful in functional imaging methods such as, blood flow measurements, increased concentration in tumor, increased accumulation in areas of brain where there is a breakdown in BBB.

The use of the probe-type imaging device of the present invention in combination with imaging agents can be advantageous when utilizing infrared excitation light for non-toxic chromophores. Specifically, such a combination can allow for the detection of the spectral signature of diseased tissue due to the fluorescence and thereafter calibrate and quantify the fluorescence spectral signature of diseased tissue.

Unique fluorescence labeled molecules like proteins, DNA and other bioactive molecules and compounds have been effectively utilized in both in vitro and ex vivo investigations. However, most of the proposed agents, methods and teaching of MFT have limited in vivo application in human imaging due to one or several of the above mentioned reasons. Therefore, more specific agents and uses are needed.

In accordance with one embodiment, the probe-type imaging device of the present invention can be used for in vivo light (e.g., fluorescence) imaging, including: 1) a specific area of imaging and/or specific fluorescent contrast media; 2) a visualization and light inspection of the intravascular device; and to select agents and methods that extend the use of light imaging to other internal organs and to MFT.

In another embodiment of the invention, the probe-type imaging device of the invention may be useful for optical intravascular visualization. The probe-type imaging device can provide light images of the intravascular lumen and walls using a variety of wavelength for emission and for several wavelengths for detection. The probe-type imaging device may also be useful where the wavelengths for light emission and detection are not the same. In such a scenario, the probe-type imaging device can provide light images in combination with a fluorescence contrast media. The probe-type imaging device of the invention may also be useful in the visualization and image analysis of lumen opening (vertical view) and wall thickness (horizontal view) displayed in real-time on the imaging and signal display screen. The probe-type imaging device of the invention may further be useful in CCD light imaging via reflection or scatter detection.

In another embodiment, the probe-type imaging device of the present invention can be used in combination with vascular contrast agents with in vivo pharmacokinetics suited for concentrating in blood or vessel wall components. Vascular contrast agents that concentrate in vascular wall components can be useful in revealing inflammation, infection, calcification, smooth muscle proliferation and/or fatty tissue accumulation as part of the plaque formation process. The probe-type imaging device of the invention may, therefore, be useful in the diagnosis of inflammation, infection, calcification, smooth muscle proliferation and/or fatty tissue accumulation as part of the plaque formation process in a subject. The probe-type imaging device of the present invention can also be used with agents designed to enhance imaging, providing fluorescence image contrast as compared to the normal vasculature, to provide diagnostic visualization of, for instance lesions, infection, plaque, thrombus cell tracking and therapy deployment in the vascular system.

Agents that use a combination detection system of positron or gamma emission on one hand and fluorescence or chemoluminescence on the other hand can take advantage of the vast knowledge developed by both technologies.

Contrast Media

Molecular imaging agents that can be used with the probe-type imaging device of the invention are similar to those described in U.S. Pat. No. 6,592,847 B1; 2003/0044353 A1; 2004/0015062 A1; U.S. Pat. No. 6,511,967 B1; 2003/017017 A1; U.S. Pat. NO. 6,319,488 B1, U.S. Pat. No. 6,403,625 B1; U.S. Pat. No. 6,630,570 B1 and references therein; as well as U.S. Pat. No. 6,630,570 B1, U.S. Pat. No. 6,319,488; and MFT U.S. Pat. No. 6,592,847 B1; 2003/0044353 A1; 2004/0015062 A1; U.S. Pat. No. 6,511,967 B1; 2003/017017 A1, all of which are incorporated herein by reference.

MFT agents may be constructed of three basic parts as follows:

Chromophores probe (e.g., a near infrared dye);
Targeting moiety (e.g., DNA, proteins, peptides); and
Delivery molecule (e.g., polymeric backbone).

MFT agents useful in imaging methods with the probe-type imaging device of the present invention can be from about 2 Kd to about 1000 Kd in size. These agents, preferably, can target specific in vivo molecular constructs, such as, light quenched probes, enzyme activity and gene expression at the targeted sites.

The methods disclosed in connection with the present invention provide protocols that may be more tissue-specific than current methods using MFT. In one embodiment, the probe-type imaging device of the invention may be used to visualize tissue with a thickness of a few microns to a few millimeters in a vessel or neoplastic tissue, as compared to several centimeters required for organ visualization in human. The invention also provides imaging methods useful to target specific cellular components of the vessel cell wall. The probe-type imaging device of the invention is not limited to the use of near infrared dyes. Agents that are constructed of the chromophores and activated chromophores (<2 KD), and chromophores that are directly attached to a targeting molecule (<2 KD), may also be useful in visualization methods utilizing the probe-type imaging device of the present invention. In certain embodiments of the invention, the molecular weight of the agents used may be smaller than 2 Kd in size. In some embodiments of the invention, molecules that are constructed of the fluorescent and/or other contrast media attached to the polymeric molecule, but without a targeting entity, may be used in combination with the probe-type imaging device of the invention. In these cases the polymeric molecule is the targeting entity and the molecular weight may be over 2 KD (no polymeric backbone). In another embodiment the probe-type imaging device of the invention may be used in combination with light emitting agents labeled with a radionuclide to allow for dual imaging detection.

Imaging agents and contrast agents particularly useful in the imaging methods of the present invention are as follows:
1. Contrast media with the following potential structure:
   pharmacophorees directly label blood components such as hemoglobin, red cells, platelets and are preincubated with blood or blood components or injected directly into a mammal; chemically activated chromophores which when contact with blood components results in a relatively stable chemical bond. The nature of this covalent bond is an interaction of the following (Table 2)
i. Free amino groups in blood proteins with a chromophores activated aster ii. Free —SH groups in blood proteins with a chromophore activated aster
iii. Exposed carboxylic groups in blood with a chromophore activated amino
iv. Blood proteins with complex with metal chromophores complexes
v. Blood components with targeted activated chromophores
vi. Other blood conjugate for imaging blood components (Table 2a)

TABLE 2

Activated fluorescent dyes for direct in vivo labeling by IV injection

| Compound | Components Labeled |
|---|---|
| Chromophore-Anhydride | Blood |
| Chromophore-Acylchloride | Blood |
| Chromophore-N-hydroxysuccinamide | Blood |
| Chromophore-Activated esters | Blood |
| Chromophore-Isothiocyanate | Blood |
| Chromophore-Melamide | Blood |

TABLE 2a

Fluorescent conjugates for blood imaging

| Compound | Components Labeled |
|---|---|
| Albumin-chromophore isothiocyanate | Blood components |
| polylysine -chromophore isothiocyanate | Blood components |
| chromophore- IgG | Blood components + Infection |
| Phalloidin-Fluorescein isothiocyanate | Blood components |
| Lectin-Fluorescein isothiocyanate | BC + glycoproteins cancer + Infection |

2. Free molecular chromophores (unattached) that have affinity to a specific tissue due to the physical, chemical or structural properties. Examples include lipophilic cationic dyes (rhodamine 123, S13, dequilinium, porphyrins) (which may not have been used specifically for imaging) and others (see list). Due to their lipophilicity and dispersed positive charge, they can concentrate preferably in certain tumor cells. Breast carcinoma cells for example, poses an enhanced negative charge on their membrane, the mitochondria has a negative charge that is stronger by 3 to 4 orders of magnitude, therefore, these dyes will concentrate preferably in these tumors. These agents have specific light activation and fluorescence properties that could be used with a specific light detector, as it would be appreciated from the description of the device. (Table 3).

TABLE 3

Chromophores for direct tissue visualization

| Fluorescent dye | MW | Indication |
|---|---|---|
| Mag-Indo-1 | 594.7 | Mg2+ |
| N,N'-bis(salicylidene) Ethylenediamine | 268.3 | Mg2+ |
| Potassium-binding benzofuran isophihalate-AM | 1171 | K+ mitochondria |
| 6-Methoxy-1-(3-sulfopropyl) quinolinium monohydrate | 281 | chloride by quenching; Measurement of membrane chloride transport |
| 9,9'-Bis(N-methylacridinium nitrate) | 510 | superoxide |
| Tris (4,7-diphenyl-1,10-phenanthrolin) ruthenium(II) dichloride complex | 1169 | oxygen probe blood and skin |

TABLE 3-continued

Chromophores for direct tissue visualization

| Fluorescent dye | MW | Indication |
|---|---|---|
| Quinones | <2 KD | melanoma and cancer |
| Rhodamine-based | <2 KD | cancer carcinoma |
| Porpherine-based | | cancer infection, inflammation |
| Dequelinium | <2 KD | cancer mitochondria |
| S13 | | cancer mitochondria |
| Tetralphenyl phosphonium based | <2 KD | blood flow |
| Amino acid color reaction reagent (DNP) | <2 KD | blood |

Chromophore=any old or novel chromophores. A chromophore as used herein means functional groups with characteristic optical absorptions or the molecules which contain them.

3. Chromophores that are bound directly or via a short tether to specific molecules that have enhanced function in the tissue of interest. I.e., chromophores attached to metabolites (fatty acids in heart, specific sugar and amino acid in tissue), ligands (with specific receptor function, hormone, alpha and beta blockers) or antibody (antigen antibody interaction). Antisense-vector-chromophore to delineate the over-expression or under-expression of gene(s) in a specific tissue. The agents proposed do not contain a polymeric construct for delivery as described in (U.S. Pat. No. 6,592,847 B1; 2003/0044353 A1; 2004/0015062 A1; U.S. Pat. No. 6,511,967 B1; 2003/017017 A1. (Table 4)

TABLE 4

Chromophores directly attached to metabolites, receptor ligands, and specific abnormal cell penetration vectors

| Agent combination | Example | Use |
|---|---|---|
| Metabolite--chromophore | omega-phenantrene-pentadecanoic acid | Heart |
| Hormone - chromophore | triphenyl-16-estradiol-phosphonium Nitrate | breast |
| Apoptotic agent - chromophore | A (6-8) amino acid trancated derivative of Anexin-V - Cyanine dye | Apeptosis |
| Blood flow agent - Chromophore | 4-chrompohphor-triphenyl phosphonium nitrate | Heart |
| Storage agent - chromophore | Aryl-guanidine - Chromophore | Brain and adrenal tumors |
| Prostate binder-chromophore | chain alkyl amine-chromophores | Prostate |
| Acetyl choline - chromophores | | |

4. For visualization with the disclosed device, the preferred agents may be plaque and plaque formation targeting molecules that can be directly attached to a fluorescent tag by a chemical bond, a tether or a complex (Table 5).

TABLE 5

Chromophores with short tether specific attachment

| Agent combination | Example | Use |
|---|---|---|
| Biotin(vector)-agent-chromophore | Biotin-antisense-chromophore | Prostate |
| Biotin-chromophore | Biotin-chromophore | Infection |
| Adenosine-chromophore | Adenosine-tether-Cyanine dye | Heart |
| Ap4Aanalog-chromophore | Ap2(Chromophore)p2A | Plaque |
| Acetylcholine receptor agonist/antagonist | RS 86 -chromophore | Alzheimer's Disease |

The following agents may also be useful in the imaging methods provided in the present invention:
1. MRI contrast media that concentrate in plaque vascular components will have different scatter and reflected light and could be used, for example Gd and Fe targeted compounds, complexes, liposome, miscelles.
2. CT contrast agents like iodinated or polyiodinated plaque targeted agents will have different scattered and reflected light therefore can be appropriate for imaging. Toxicity is less of a problem than MRI.
3. Fluorescence and chemoluminescence agents (Tables 2-4).

These agents may be particularly useful when the light viewing with the probe-type imaging device is used in combination with other imaging modalities.

References

The contents of all art referenced in this patent application are incorporated herein in their entireties.
Microlens for detector: Wu M H, Paul K E, Whitesides G M. 2002. Patterning flood illumination with microlens arrays. Appl. Opt. May 1; 41(13):2575-85.
Single photon emitter as light source: Gudiksen M S, Lauhon L J, Wang j, Smith D C, Lieber C M. 2002. Growth of nanowire superlattice structures for nanoscale photonics and electronics. Nature. Feb 7; 415(6872): 617-20.
Diffuse light scattering for theory: Butler J M, Miki H, Squarcia S, Rogers R A, Lehr J L. 1996. Effect of macroscopic deformation on lung microstructure. J. Appl. Physiol. 81(4):1792-99.

EXAMPLES

It will be expressly understood that the examples provided hereinafter are merely representative of the possible embodiments of the invention, and that these examples are the illustrative of the far greater range of formats which are potentially possible and useful within the invention.

Example 1

Imaging of Rabbit Aorta

Figure 17:
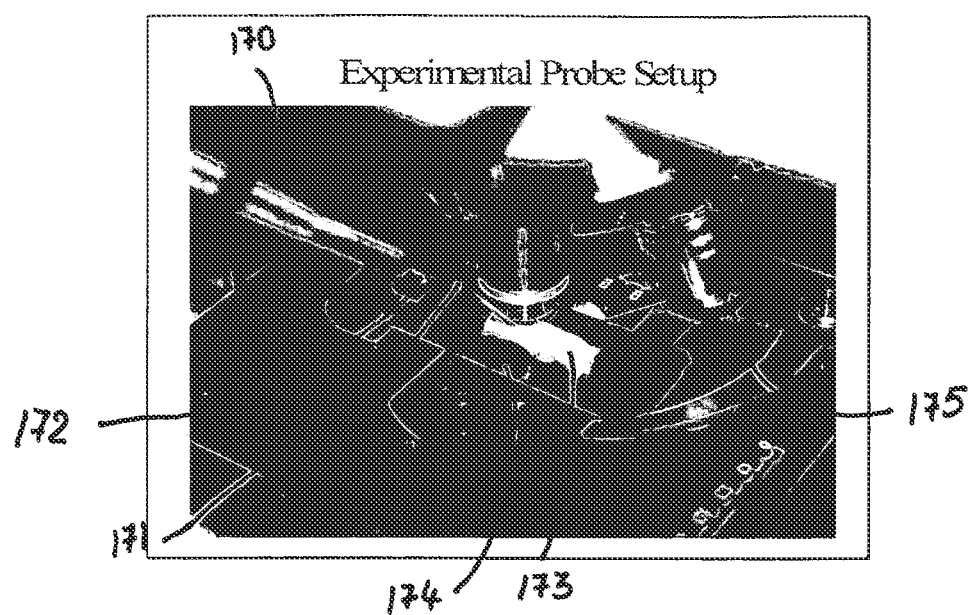
FIG. 17 illustrates a an experimental probe setup. Drinking straw (Left) contains a double fiber optic probe held by a mechanical positioner. Rabbit aorta pinned to a flexible base placed on a microscope. A 10× objective was used to collect scattered light from delivery fiber (wavelengths >540 nm).
Figure 18:
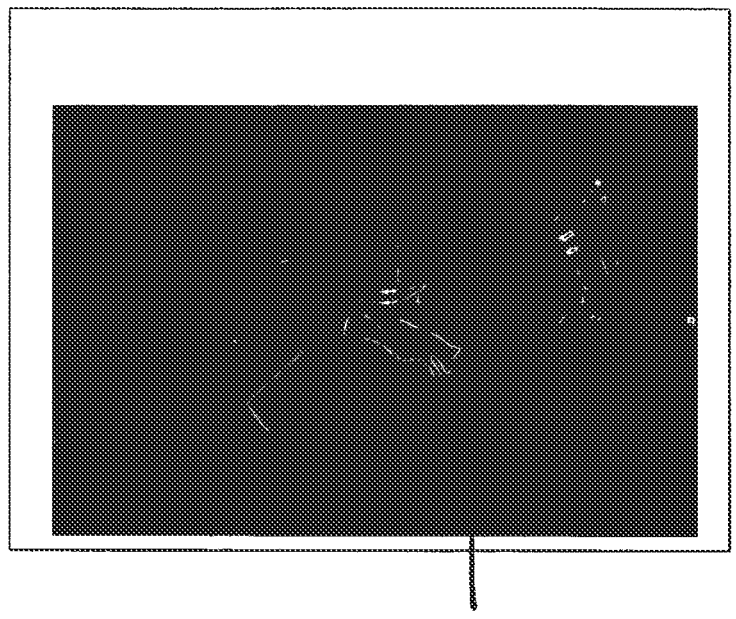
FIG. 18 illustrates another experimental probe setup.

A working scattered-light prototype of the probe-type imaging device was demonstrated using excised pieces of rabbit aorta and a modified confocal microscope. FIG. 17 illustrates an experimental probe setup. The drinking straw 170 (left) contained a double fiber optic probe 171 held by a mechanical positioner 172. Rabbit aorta 173 was pinned to a flexible base 174 placed on a microscope 175. A 10× objective was used to collect scattered light from delivery fiber 171 (wavelengths >540 nm). Although crude in construction (drinking straw, double fiber optic probe held by a mechanical positioner) the device records measurable differences in diffusely scattered light collected by a 10× objective at wavelengths greater than 510 nm. As shown in FIG. 18 light was delivered to the luminal surface of aorta 173. Scattered light was detected 10's of microns away from probe tip.

Figure 19:
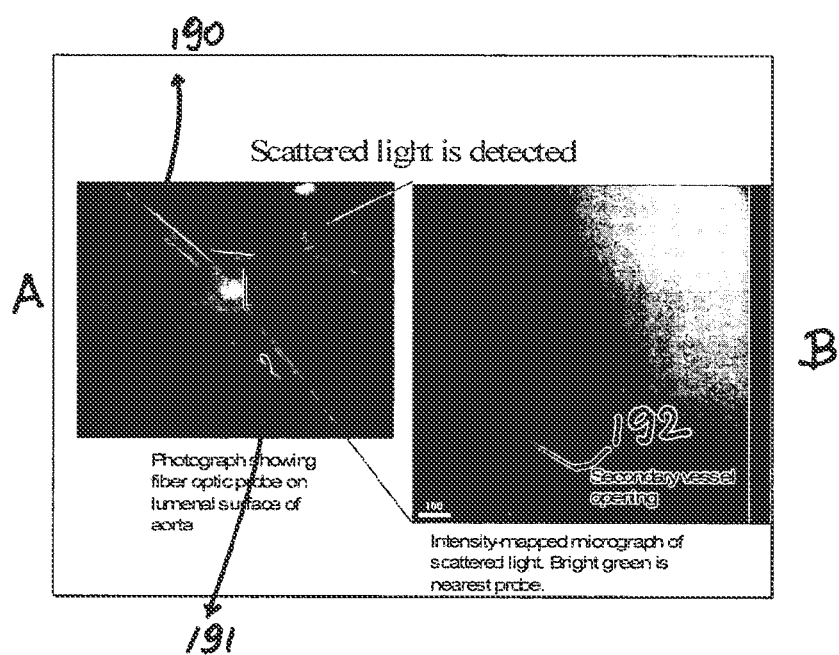
FIGS. 19 A-B illustrate vessel tissue obtained using a probe-type imaging device of the invention.

FIGS. 19A-B, illustrate visualization of vessel tissue obtained by placing the probe-type imaging device 190 on the vessel luminal surface 191. FIG. 19A illustrates a fiber-optic probe 190 on the luminal surface of aortic tissue 191. FIG. 19B illustrates an intensity graph micrograph of scattered light around a secondary vessel, e.g., lumen 192 (darker region). As shown in FIGS. 19A-B, scattered light diffusely escaping from tissue revealed a detectable and measurable signal. Lumens 192 from secondary vessels remain dark and distinguishable.

Figure 20:
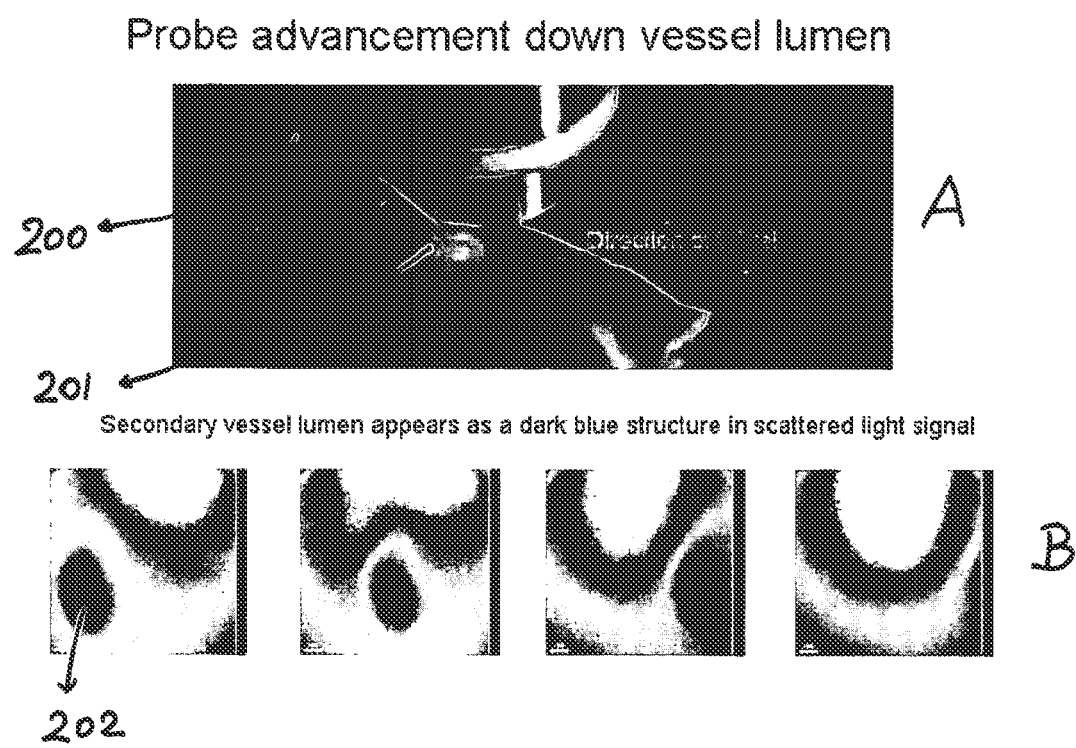
FIG. 20A illustrates an experimental setup showing a probe-type imaging device of the invention being advanced down a vessel lumen.
FIG. 20B illustrates light intensity micrographs obtained from a probe-type imaging device of the invention being advanced down a vessel lumen showing scattered light around a secondary vessel (darker region).

FIGS. 20A-B illustrate visualization of vessel tissue obtained by advancing the probe-type imaging device along a vessel luminal surface. FIG. 20A, illustrates an experimental setup showing a probe-type imaging device 200 of the invention being advanced down a vessel lumen 201. FIG. 20B shows in series light intensity micrographs obtained from a probe-type imaging device 200 of the invention being advanced down a vessel lumen showing scattered light around a secondary vessel 202 (darker region). Scattered light detection showed alterations of vessel wall features the probe is advanced along the vessel luminal surface.

Figure 21:
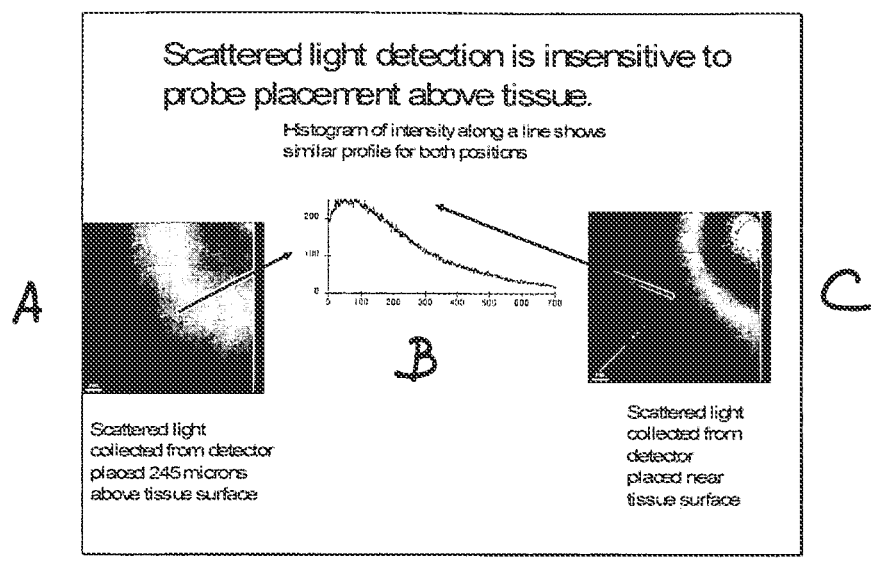
FIG. 21A is an image of scattered light collected from a probe-type imaging device of the invention placed 245 microns above a tissue surface.
FIG. 21B is a graph showing the intensity of scattered light collected from a probe-type imaging device of the invention as a function of distance from a tissue surface.
FIG. 21C is an image of scattered light collected from a probe-type imaging device of the invention placed near a tissue surface.

As shown in FIGS. 21A-C, a signal obtained from the probe-type imaging device was not sensitive to probe proximity to vessel wall surface. FIG. 21A, is an image of scattered light collected from a probe-type imaging device of the invention placed 245 microns above a tissue surface. FIG. 21B, is a graph showing the intensity of scattered light collected from a probe-type imaging device as a function of distance from a tissue surface. FIG. 21C, is an image of scattered light collected from a probe-type imaging device of the invention placed near a tissue surface. As detailed in FIGS. 21A-C, the light signal detected from vessel wall was insensitive to illumination source above vessel wall surface.

Figure 22:
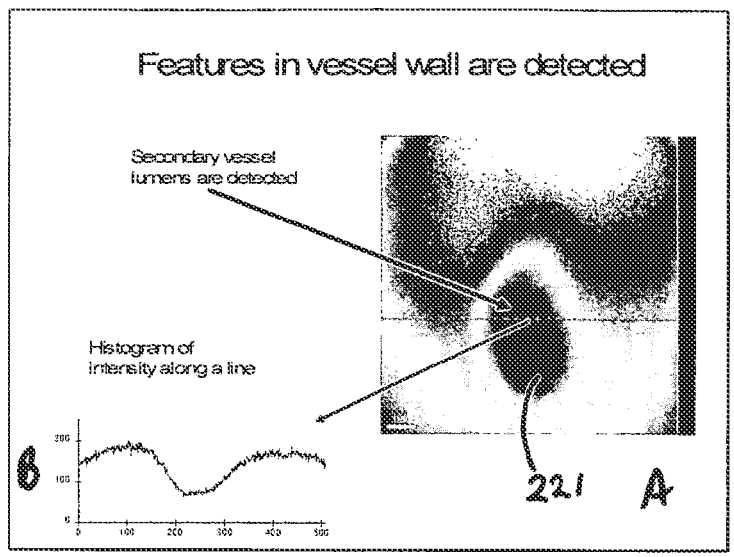
FIG. 22A illustrates an intensity graph micrograph of scattered light around a secondary vessel (darker region).
FIG. 22B illustrates a graph showing the relative scattered light intensity signal observed around a secondary vessel using the probe-type imaging device of the invention.

As detailed above and further illustrated in FIGS. 22A-B, features in the vessel wall were detected in scattered light detection mode. Variations in light intensity tracked with physical changes in vessel wall. FIG. 22A, illustrates an intensity micrograph of scattered light around a secondary vessel 221 (darker region). FIG. 22B, is a graph showing the relative scattered light intensity signal observed around a secondary vessel using the probe-type imaging device of the invention.

Figure 23:
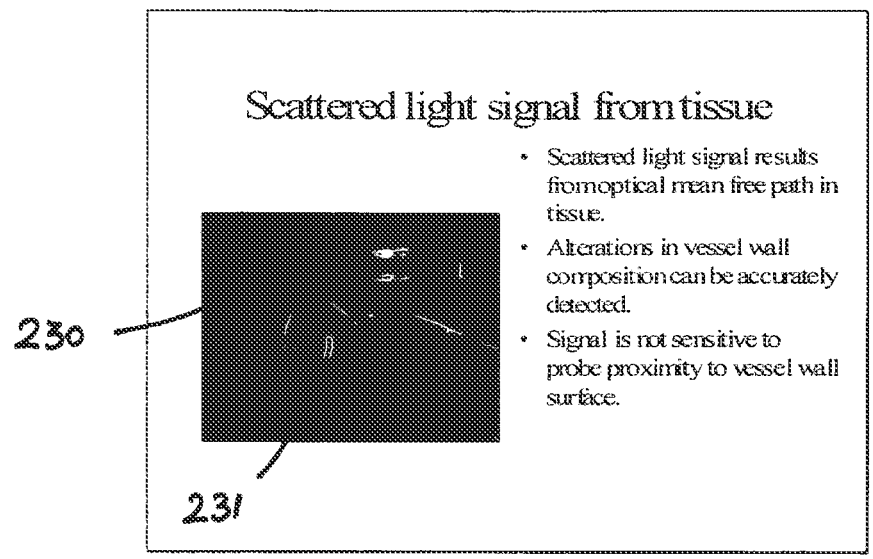
FIG. 23 illustrates an experimental setup showing a probe-type imaging device of the invention being advanced down a vessel lumen.

FIG. 23 illustrates an experimental setup showing a probe-type imaging device 230 of the invention being advanced down a vessel lumen 231. Diffuse scattered light was derived from the detection of the mean free optical path of photons escaping from tissue.

Example 2

Imaging of Diseased and Normal Rabbit Aorta Tissue Regions

Figure 24:
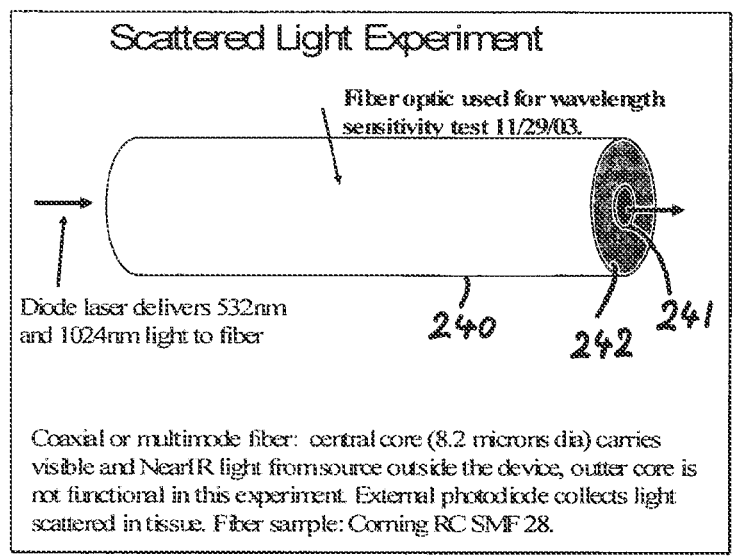
FIG. 24 is a schematic diagram showing a probe-type imaging device of the invention wherein illumination light delivered to tissue is carried in a single mode fiber with a central core of less than 9 microns used to deliver light to tissue.

Light intensities detected from diseased and normal regions of rabbit aorta were examined using light from 488 nm fluorescent light, 532 nm and 1024 nm light from a solid state diode source as illustrated in FIG. 24. Shown in FIG. 24 illumination light was delivered to tissue via a single mode fiber 240 with a central core 241 of less than about 9 microns. A photodiode 242 placed near the fiber tip collected scattered and reflected light from the tissue.

Figure 25:
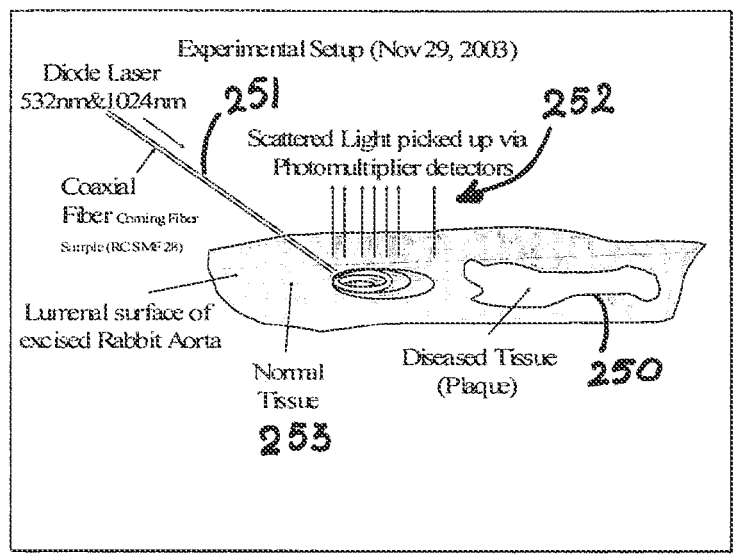
FIG. 25 is a schematic diagram of an experimental setup used to demonstrate scattered light imaging.

FIG. 25 is a schematic diagram of an experimental setup used to demonstrate scattered light imaging. A diseased experimental piece of aorta 250 was placed on microscope stage. A fiber optic imaging probe 251 was placed parallel, or at an oblique angle to the lumen surface. Light from a diode laser (not shown) passing through the fiber 251 illuminated a local region at the fiber end. Multiple photodetectors 252 placed above the fiber end detected the light (same frequency) scattered from the surrounding tissue 253. Diseased tissue 250 was identified by changes of light intensity and distance from the probe 251 tip. Intensity of back scattered light ($\lambda$) at various distances r from the point of entry of light, and the product of $Ir^3$ was plotted semi logarithmically against r. The fractional change in optical mean free path (λ) were determined from the following equation (δ λ/λ=(11+2rs)−1δ F(r, λ) as referenced in the paper: Miki H, Rogers R A, Lehr J, Butler J P. Geometric hysteresis in pulmonary surface-to-volume ratio tidal breathing. J Appl Physiol 1993; 75(4): 1630-1636.

Figure 26:
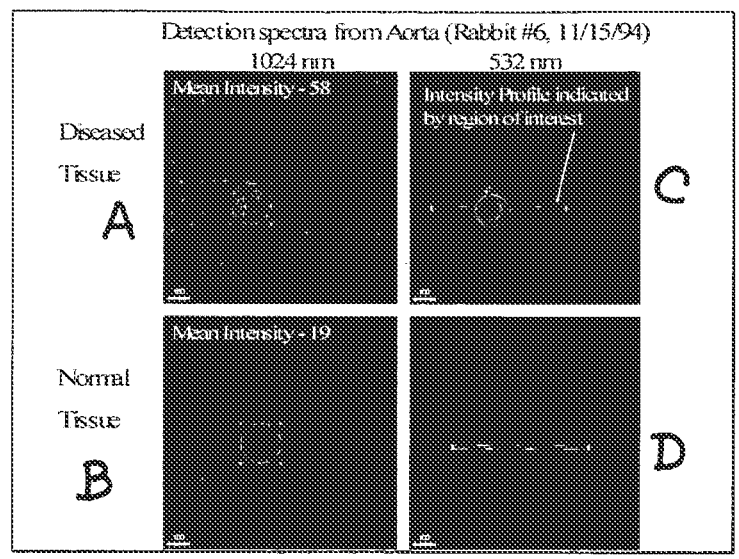
FIG. 26A illustrates an intensity graph micrograph of scattered light from diseased rabbit aortic tissue as detected using a single mode fiber with a central core emitting light at 1024 nm wavelength.
FIG. 26B illustrates showing an intensity graph micrograph of scattered light from normal rabbit aortic tissue as detected using a single mode fiber with a central core emitting light at 1024 nm wavelength.
FIG. 26C illustrates an intensity graph micrograph of scattered light from diseased rabbit aortic tissue as detected using a single mode fiber with a central core emitting light at 532 nm wavelength.
FIG. 26D illustrates an intensity graph micrograph of scattered light from normal rabbit aortic tissue as detected using a single mode fiber with a central core emitting light at 532 nm wavelength.
Figure 27:
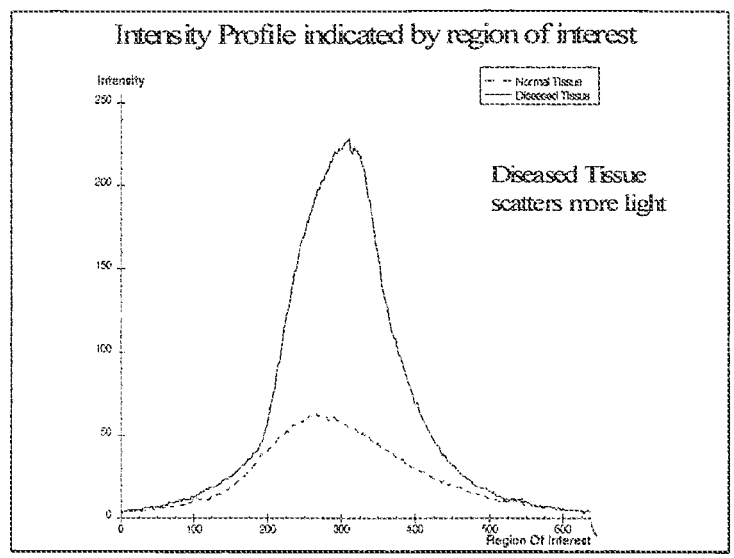
FIG. 27 is a graph of the light intensity profile of diseased and normal tissue as determined using a single mode fiber with a central core emitting light at 532 nm or 1024 nm wavelength.

Detection spectra observed from diseased and normal regions of rabbit aorta are shown in FIG. 26A-D. FIG. 26A, is a photograph showing an intensity graph micrograph of scattered light from diseased rabbit aortic tissue as detected using a probe-type imaging device emitting light at 1024 nm wavelength. FIG. 26B, is a photograph showing an intensity graph micrograph of scattered light from normal rabbit aortic tissue as detected using a probe-type imaging device emitting light at 1024 nm wavelength. FIG. 26C, is a photograph showing an intensity graph micrograph of scattered light from diseased rabbit aortic tissue as detected using a probe-type imaging device emitting light at 532 nm wavelength. FIG. 26D, is a photograph showing an intensity graph micrograph of scattered light from normal rabbit aortic tissue as detected using a probe-type imaging device emitting light at 532 nm wavelength. Light from both the 532 nm light source and the 1024 nm tight source exhibited a higher mean intensity in diseased tissue than light scattered from normal tissue. Regions of interest were indicated and pixel intensities were plotted on the graph shown in FIG. 27. FIG. 27 is a graph of the light intensity profile of diseased and normal tissue as determined using one embodiment of a probe-type imaging device. The graphical representation on the pixel intensities as a function of the region of interest confirmed that the light from both the 532 nm light source and the 1024 nm light source exhibited a higher mean intensity in diseased tissue than light scattered from normal tissue.

Equivalents

Although particular embodiments have been disclosed herein in detail, this has been done by way of example for purposes of illustration only, and is not intended to be limiting with respect to the scope of the appended claims which follow. In particular, it is contemplated by the inventor that substitutions, alterations, and modifications may be made to various features of the invention without departing from the spirit and scope of the invention as defined by the claims. For instance, the selection of the photonic detector pattern and type as well as the imaging agent is considered within the skill of the ordinary artisan.

What is claimed is:

1. A vascular system and/or blood optical imaging system comprising:
   an intravascular optical imaging probe configured for optically imaging one or both of in vivo blood and/or an in vivo vascular system, and,
   a optical imaging agent configured for co-acting with the intravascular optical imaging probe for optically imaging one or both of in vivo blood and/or an in vivo vascular system, the optical imaging agent comprising:
      a single optical imaging chromophore with a single tether to a specific targeting molecule having enhanced function in optical imaging in an in vivo tissue of interest, the tissue of interest being one or more of in vivo blood, an in vivo blood component or an in vivo vascular system;
      each combination of an optical imaging chromophore and tether and targeting molecule having a combined molecular weight of less than 2 KD,
      the tether being short (—CH$_2$(CH$_2$)$_n$-; n=1-10) or a limited MW polylysine or a peptide and having enhanced functionality in optical imaging beyond tethering and being used in in vivo intravascular optical imaging;
   the targeting molecule including one of:
   Anhydride
   Acylchloride
   N-hydroxysuccinamide
   Activated esters
   Isothiocyanate
   Melamide
   IgG
   metabolite,
   receptor ligands,
   activated amino
   specific abnormal cell penetration vectors
   metabolite
   omega-phenantrene pentadecanoic acid
   Hormone
   triphenyl-16-estradiol-phosphonium Nitrate
   Apoptotic agent
   A (6-8) amino acid truncated derivative of Anexin-V
   Blood flow agent
   4-chrompohphor-
   triphenyl phosphonium nitrate
   Storage agent
   Aryl-guanidine
   Prostate binder-
   chain alkyl amine-
   Acetylcholine
   Biotin(vector)-agent-
   Biotin-antisense-
   Biotin-
   Adenosine
   Ap4Aanalog-
   Ap2(Chromophore)p2A
   Acetylcholine receptor
   RS 86;
      wherein the combined optical imaging chromophore, tether and targeting molecule are one or more of disposed and configured to:
         be injected into an in vivo subject,
         move through the blood system in the blood of the in vivo subject,
         target a specific in vivo tissue of interest in a subject, the in vivo tissue of interest being one or more of in vivo blood, an in vivo blood component or an in vivo vascular system and
         attach to the specific in vivo tissue in a subject without damage thereto and provide optical imaging contrast for and in coaction with the intravascular optical imaging device;
   wherein the optical imaging agent comprises one or more of:
      chromophore-anhydride, chromophore-acylchloride, chromophore-Nhydroxysuccinamide, chromophore-activated esters, chromophore-isothiocyanate, chromophore-melamide, albumin-chromophore isothiocyanate, polylysine-chromophore isothiocyanate, chromophore-IgG, palloidin-fluorescein isothiocyanate, lectinflourescein isothiocynate, lipophilic cationic dyes, mag-indo-1N,N'-bis(salicylidene), ethylenediamine, potassium binding benzofuran isophthalate-AM, 6-methoxy-1-(3-aulfopropyl) quinolinium monohydrate, 9,9'-bis(N-methylacridinium nitrate), tris(4,7-dipheyl-1,10-phenanthrolin) ruthenium(11) dichloride complex, quinones, rhodamine-based, porpherine-based, dequelinium, S 13, tetralphenyl phosphonium-based, amino acid color reaction reagent (DNP), metabolite-chromophore, hormone-chromophore, apoptotic agent-chromophore, blood flow agent-chromophore, storage agent-chromophore, prostate binder-chromophore, acetylcholine-chromophore, biotin (vector)-agent-chromophore, biotin-chromophore, ap4analog-chromphore, and acetylcholine receptor agonist/antagonist.

2. A vascular system and/or blood optical imaging system according to claim 1 wherein the optical imaging chromophore is capable of labeling a blood component including hemoglobin, red blood cells and platelets.

3. A vascular system and/or blood optical imaging system as set forth in claim 1, wherein the optical imaging agent includes a free molecular optical imaging chromophore having affinity to a specific tissue through one of physical, chemical, or structural properties.

4. A vascular system and/or blood optical imaging system as set forth in claim 1, wherein the optical imaging agent includes an optical imaging chromophore attached to one of metabolites, receptor ligands, and specific abnormal cell penetration vectors.

* * * * *